US007091508B2

(12) United States Patent
Goldstein

(10) Patent No.: US 7,091,508 B2
(45) Date of Patent: *Aug. 15, 2006

(54) RADIATION PROTECTION SYSTEM

(75) Inventor: James A. Goldstein, Bloomfield Hill, MI (US)

(73) Assignee: ECO Cath-Lab Systems, Inc., Bloomfield Hills, MI (US)

( * ) Notice: Subject to any disclaimer, the term of this patent is extended or adjusted under 35 U.S.C. 154(b) by 31 days.

This patent is subject to a terminal disclaimer.

(21) Appl. No.: 10/721,032

(22) Filed: Nov. 24, 2003

(65) Prior Publication Data

US 2004/0161076 A1    Aug. 19, 2004

Related U.S. Application Data

(60) Division of application No. 09/990,073, filed on Nov. 21, 2001, now Pat. No. 6,653,648, which is a continuation-in-part of application No. 09/638,772, filed on Aug. 15, 2000, now Pat. No. 6,448,571.

(51) Int. Cl.
G21F 3/00    (2006.01)
(52) U.S. Cl. .................................. 250/515.1; 378/160
(58) Field of Classification Search .............. 250/515.1
See application file for complete search history.

(56) References Cited

U.S. PATENT DOCUMENTS

| 1,907,523 | A |   | 5/1933  | Egressi et al.  |
|-----------|---|---|---------|-----------------|
| 3,299,270 | A |   | 1/1967  | D'Avella        |
| 3,308,297 | A |   | 3/1967  | Mansker         |
| 3,904,695 | A |   | 9/1975  | Hendrickx et al.|
| 3,924,374 | A |   | 12/1975 | Volper          |
| 4,062,518 | A |   | 12/1977 | Stivender et al.|
| 4,074,141 | A |   | 2/1978  | Bryant          |
| 4,400,623 | A |   | 8/1983  | Jacobson        |
| 4,460,833 | A |   | 7/1984  | Malamud et al.  |
| 4,510,939 | A |   | 4/1985  | Brenman et al.  |
| 4,514,640 | A |   | 4/1985  | Bagnell et al.  |
| 4,581,538 | A | * | 4/1986  | Lenhart ................... 250/519.1 |
| 4,638,166 | A |   | 1/1987  | Baudro          |
| 4,729,869 | A |   | 3/1988  | Schukei et al.  |
| 4,905,265 | A |   | 2/1990  | Cox et al.      |
| 4,938,233 | A |   | 7/1990  | Orrison, Jr.    |
| 4,977,585 | A |   | 12/1990 | Boyd et al.     |
| 4,982,744 | A |   | 1/1991  | Stanec          |

(Continued)

FOREIGN PATENT DOCUMENTS

DE    1128950 B    5/1962

OTHER PUBLICATIONS

Livingston, "Obesity and Its Surgical Management," Am. J. Surg., 2002, pp. 103-113, vol. 184.

(Continued)

Primary Examiner—John R. Lee
Assistant Examiner—Phillip A. Johnston
(74) Attorney, Agent, or Firm—Sonnenschein Nath & Rosenthal LLP

(57) ABSTRACT

A method of performing a medical procedure includes providing a radiation-shielding cubicle having an interior defining a medical personnel region and including a first wall having an opening therein, locating the cubicle with respect to an x-ray table so a portion of the x-ray table extends through the opening into the interior of the cubicle, and separating medical personnel from an x-ray emitter disposed outside of the cubicle using the first wall to shield the medical personnel from radiation emitted by the x-ray emitter.

13 Claims, 9 Drawing Sheets

U.S. PATENT DOCUMENTS

| | | |
|---|---|---|
| 5,006,718 A | 4/1991 | Lenhart |
| 5,029,941 A | 7/1991 | Twisselmann |
| 5,090,044 A | 2/1992 | Kobayashi |
| 5,138,138 A | 8/1992 | Theilacker et al. |
| 5,417,225 A | 5/1995 | Rubenstein et al. |
| 5,442,729 A | 8/1995 | Kramer et al. |
| 5,483,562 A | 1/1996 | Kornfeldt et al. |
| 5,490,716 A | 2/1996 | Naughton |
| 5,506,882 A | 4/1996 | O'Farrell, Jr. et al |
| 5,564,438 A | 10/1996 | Merchant |
| 5,586,163 A | 12/1996 | Goldstein |
| 5,613,254 A | 3/1997 | Clayman et al. |
| 5,632,275 A | 5/1997 | Browne et al. |
| 5,636,259 A | 6/1997 | Khutoryansky et al. |
| 5,842,987 A | 12/1998 | Sahadevan |
| 5,851,182 A * | 12/1998 | Sahadevan .................. 600/407 |
| 5,980,472 A | 11/1999 | Seyl |
| 5,981,964 A | 11/1999 | McAuley et al. |
| 5,994,706 A | 11/1999 | Allen et al. |
| 6,023,799 A | 2/2000 | Wirth et al. |
| 6,104,779 A | 8/2000 | Shepherd |
| 6,105,578 A | 8/2000 | Sommers et al. |
| 6,224,548 B1 | 5/2001 | Gopinathan et al. |
| 6,248,064 B1 | 6/2001 | Gopinathan et al. |
| 6,282,264 B1 | 8/2001 | Smith et al. |
| 6,325,538 B1 * | 12/2001 | Heesch ....................... 378/203 |
| 6,334,852 B1 | 1/2002 | Seyl |
| 6,448,571 B1 | 9/2002 | Goldstein |
| 6,463,701 B1 | 10/2002 | Baloga |
| 6,520,940 B1 | 2/2003 | Gomez |
| 6,595,918 B1 | 7/2003 | Gopinathan et al. |
| 6,653,648 B1 | 11/2003 | Goldstein |

OTHER PUBLICATIONS

Podnos et al., "Complications After Laparoscopic Gastric Bypass," Arch. Surg., 2003, pp. 957-961, vol. 138.

Stocker, "Management of the Bariatric Surgery Patient," Endocrinol. Metab. Clin. N. Am., 2003, pp. 437-457, vol. 32.

Nuclear Associates, "Clear-Pb Lead-Plastic Multipurpose Adjustable-Height Mobile Barrier," 2000, 6 pages, New Jersey, U.S.A.

Worldwide Innovations & Technologies, Inc., "Breakthrough Technology in Radiation Protection," 3 pages, Kansas, U.S.A.

Randall et al., "Neuro-Oncology Update: Radiation Safety and Nursing Care During Interstitial Brachytherapy," J. Neuroscience Nursing, 1987, vol. 19.

Sewchand et al., "Radiation Control in the Intensive Care Unit for High Intensity Iridium-192 Brain Implants," Neurosurgery, p. 584, vol. 20.

Ross et al., "Prevalence of Spinal Disc Disease Among Interventional Cardiologists," Am. J. Cardiology, 1997, vol. 79.

Clark, "Editorial Comment: How Much is Too Much?," Catheterization and Cardiovascular Interventions, 2000, p. 285, vol. 51.

Balter, "An Overview of Radiation Safety Regulatory Recommendations and Requirements," Catheterization and Cardiovascular Interventions, 1999, pp. 469-474, vol. 47.

* cited by examiner

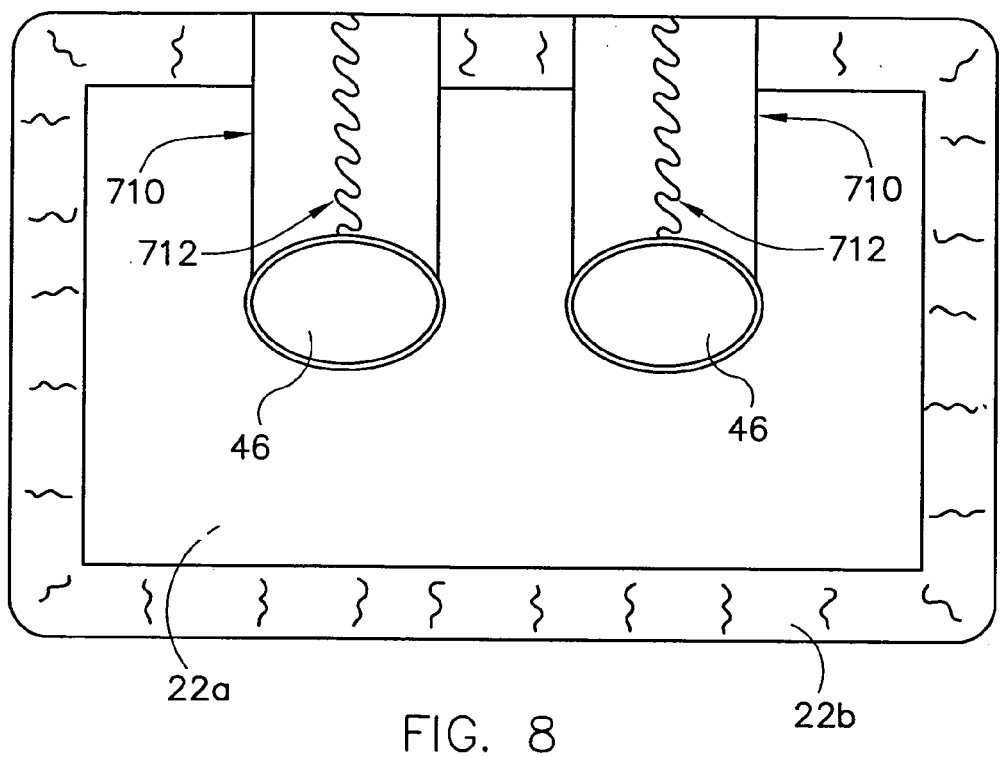
FIG. 8
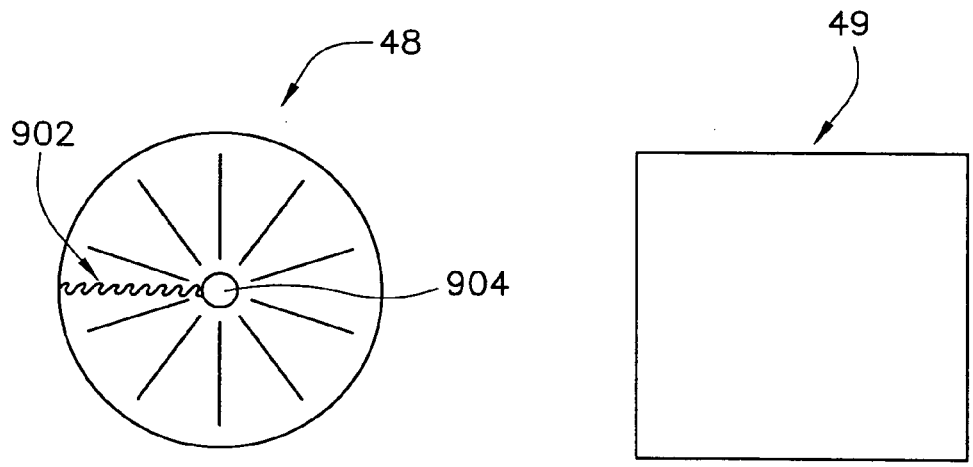
FIG. 9A
FIG. 9B

RADIATION PROTECTION SYSTEM

PRIORITY STATEMENT

This application is a divisional of U.S. application Ser. No. 09/990,073 filed Nov. 21, 2001, now U.S. Pat. No. 6,653,648 which is a continuation-in-part of U.S. application Ser. No. 09/638,772 filed Aug. 15, 2000, now U.S. Pat. No. 6,448,571, which are incorporated herein by reference to the extent permitted by law.

FIELD OF THE INVENTION

This invention relates generally to radiation protection systems and, more particularly, to radiation shielding systems with integrated procedural environments for use in the course of diagnostic or therapeutic procedures as well as methods for the use of such systems.

BACKGROUND OF THE INVENTION

X-rays are used in a wide variety of medical procedures, many of which require medical personnel to be in direct contact with the patient, thereby exposing such personnel to radiation.

As presently configured, x-ray laboratories produce x-ray exposure to the patient and to the operator and associated technicians. Since patients undergo a limited number of exposures, cumulative radiation exposure to the individual patient is rarely a significant health concern. However, operators and health care personnel performing numerous procedures per year over many years may be exposed to significant cumulative radiation doses over time, which may have adverse effects. See David A. Clark, *Editorial Comment*, 51 Catheterization and Cardiovascular Interventions 265 (2000); Stephen Balter, *An Overview of Radiation Safety Regulatory Recommendations and Requirements*, 47 Catheterization and Cardiovascular Interventions 469 (1999).

For this reason, both fixed and mobile lead shields are employed in fluoroscopic procedures to minimize radiation exposure. Such shields typically are constructed of radiation resistant plates suspended on bars that are adjusted to be interposed between the operators and the patient on the x-ray table. Despite the use of these shields, medical personnel are still exposed to radiation. It is therefore imperative that personnel wear leaded protective clothing (including full lead aprons, thyroid collars and leaded glasses). In addition, the doctors or other operators perform these radiologic procedures many hours per day and several days per week over many years throughout their medical careers. This long term, cumulative exposure may cause adverse effects. Furthermore, the wearing of heavy lead aprons may have long term deleterious effects resulting in disabling disorders of the spine in a significant number of operators. See Allan Mr. Rose, et al., *Prevalence of Spinal Disc Disease Among Interventional Cardiologists*, 79 American Journal of Cardiology 68 (1997).

There are patents teaching systems for protecting and shielding against radiation in x-ray laboratories. The patents describe various shields made of radiation resistant material that are either mobile or attached to the x-ray table and can be adjusted between the operators and the x-ray source. Though there are numerous shapes and designs for these shields, and although they may be constructed of various materials, they do not sufficiently protect against radiation exposure, and medical personnel must still wear heavy and encumbering leaded protective clothing. Furthermore, such leaded protective aprons, collars and glasses do not fully protect the operator as they leave substantial portions of legs, arm and head exposed.

Despite dramatic technological evolution of the imaging systems employed for diagnostic and therapeutic radiological procedures, the fundamental architecture of the radiological x-ray laboratory and its ancillary components have not changed appreciably over the last 50 years. For example, in the present configuration of a typical cardiac catheterization laboratory, there is a fixed floor or ceiling mounted radiological C-arm along with the ancillary electrical and computer equipment necessary to run the x-ray system. However, in order to perform diagnostic and therapeutic procedures, such a laboratory requires multiple other capital equipment items, as well as disposables. These items may include a fluoroscopy table, manual controls for the table, fluoroscopy monitors positioned some distance away from the procedure site and out of the operator's preferred line of site, physiological sensors and instruments for monitoring the patient, at least one staging area often located behind the surgeon or at the patient's groin area, and various other surgical tools and medical disposables. In the present configurations, neither these items nor the laboratory itself are optimized for procedural efficiency or radiation protection of the medical personnel within the laboratory.

When working with a patient on an x-ray table, doctors and other medical personnel can be exposed to primary radiation that emanates directly from the source or can be exposed to secondary radiation that is reflected or scattered by an object such as the x-ray detector, the x-ray table, and even the patient. No prior invention has sufficiently reduced the primary and secondary radiation exposure of operators in an x-ray laboratory and addressed its inefficiencies of such a lab by using a radiation protection system comprising a shielding cubicle, screen, flexible interface and integrated operations environment.

SUMMARY OF INVENTION

In one aspect, a method is provided of performing a medical procedure. The method includes providing a radiation-shielding cubicle having an interior defining a medical personnel region and including a first wall having an opening therein, locating the cubicle with respect to an x-ray table so a portion of the x-ray table extends through the opening into the interior of the cubicle, and separating medical personnel from an x-ray emitter disposed outside of the cubicle using the first wall to shield the medical personnel from radiation emitted by the x-ray emitter.

In another aspect, a method is provided of using a radiation protection system including an x-ray table having a top surface for supporting a patient and a radiation-shielding screen attached to the x-ray table for covering a portion of the patient and a portion of the top surface of the x-ray table, wherein the radiation-shielding screen includes at least one port. The method includes extending the radiation-shielding screen over a portion of the patient supported by the top surface of the x-ray table, inserting procedural equipment through the port to access the patient with the procedural equipment, and performing a medical procedure on the patient using the procedural equipment.

In even another aspect, a method is provided of performing a medical procedure. The method includes providing a radiation-shielding wall having an opening therein, locating the wall with respect to an x-ray table so a portion of the x-ray table extends through the opening, joining the x-ray table to the wall using a radiation-shielding flexible interface, sealing the opening in the first wall using a flexible radiation-resistant skirt, and using the wall to separate medical personnel located adjacent a first side of the wall from an x-ray emitter disposed adjacent a second side of the wall opposite the first side to shield the medical personnel from radiation emitted by the x-ray emitter.

In yet another aspect, a method is provided of using a radiation protection system including an x-ray table having a top surface for supporting a patient, a radiation-shielding screen attached to the x-ray table for covering a portion of the patient and a portion of the top surface of the x-ray table, and controls for controlling the system, wherein the radiation-shielding screen includes at least one port. The method includes extending the radiation-shielding screen over a portion of the patient supported by the top surface of the x-ray table, accessing the controls through the port, and controlling the system using the controls.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 8 illustrates a top-view of a radiation resistant screen of the present invention;

FIGS. 9A and 9B show two access port covers of the present invention; and

DETAILED DESCRIPTION OF PREFERRED EMBODIMENT

Figure 1:
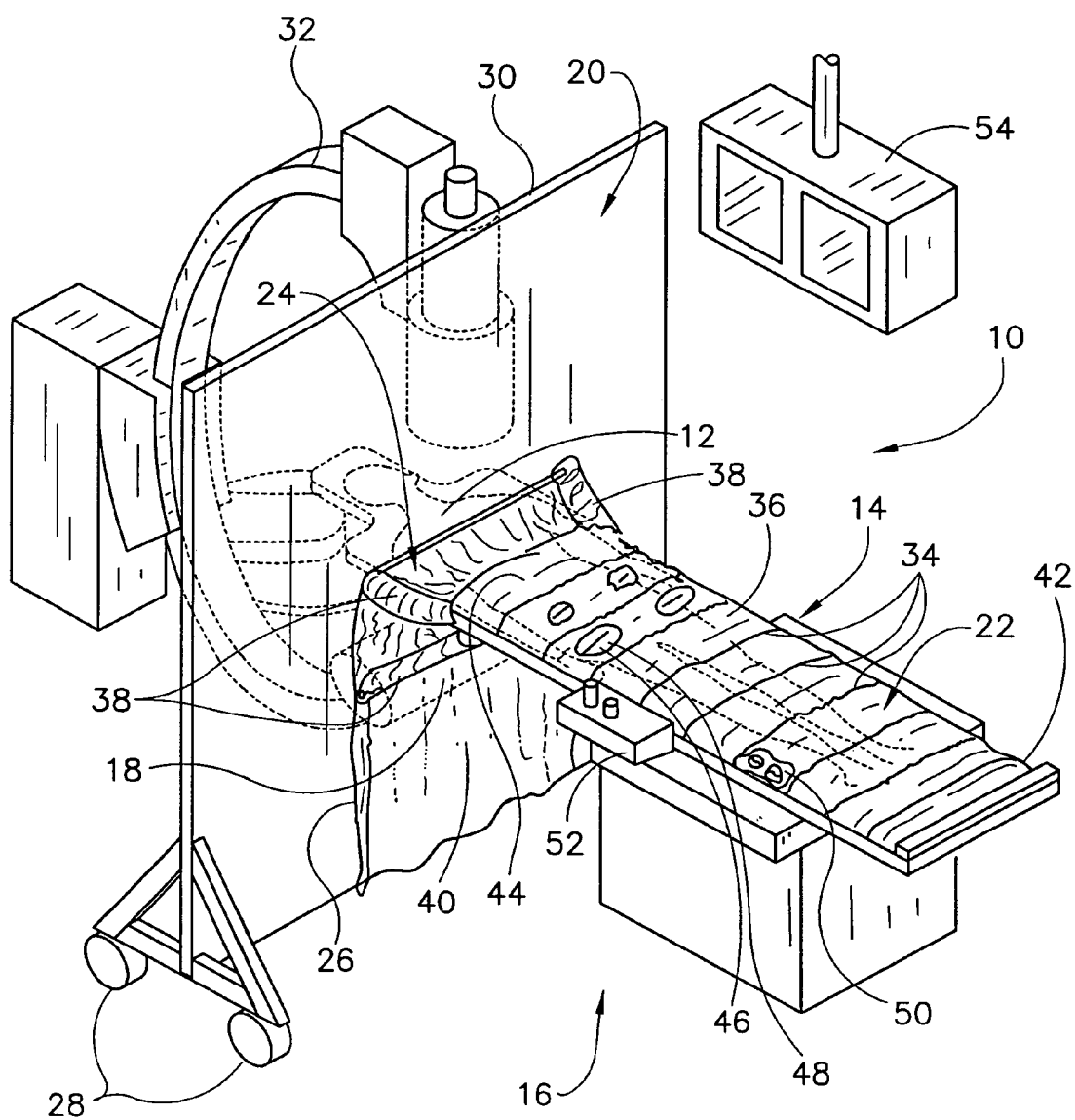
FIG. 1 illustrates a perspective view of a radiation protection system according to the present invention.

Referring to the accompanying drawings in which like reference numbers indicate like elements, FIG. 1 illustrates a radiation protection system 10 that covers a patient 12 on an x-ray table 14 and separates an operating region 16 from a C-arm x-ray emitter 18. The radiation protection system 10 includes a radiation-shielding wall 20, a radiation-shielding screen 22 on the x-ray table, and a radiation-shielding flexible interface 24 connecting the screen 22 and x-ray table 14 with the wall 20. The wall 20 is constructed from well-known radiation-blocking materials and is preferably transparent, thereby permitting visual contact between operators (not shown) in the medical personnel region 16 and the patient 12. An opening 26 is provided in the wall 20 so that it can be moved over the x-ray table 14. A mobility device, such as casters 28 or tracks (not shown) permits the wall 20 to be rolled into place, and retracting the casters 28 sets the wall in place. The top of the wall 30 is preferably higher than the C-arm 32 at its highest extension.

The radiation-shielding screen 22 is movably attached to the x-ray table 14. The screen 22 may have a plurality of screen supports 34 (see also FIG. 6) attached to the x-ray table 14 and a radiation-resistant partition 36 attached to the supports 34. When extended, the screen 22 covers the x-ray table 14 in the personnel region 16 and the partition 36 is interposed between the patient 12 and the operators. The flexible interface 24 may have flexible joints 38 and a flexible, radiation-resistant skirt 40. The flexible joints 38 connect the wall 20 with the x-ray table 14 and hold the skirt 40. The skirt 40 joins the wall 20 to the screen 22 and covers the opening 26 in the wall. The flexible joints 38 and skirt 40 may extend, thereby allowing movement of the x-ray table 14 during the medical procedure without moving the wall 20. Thus, the connections between the screen 22, table 14, interface 24 and wall 20 (or cubicle 100 in other embodiments) creates a radiation-resistant seal.

Transferring the patient 12 to and from the x-ray table 14 is facilitated by detaching the flexible interface 24 from the wall 20 and moving the wall, and by retracting the screen 22 to the foot 42 of the x-ray table 14. During fluoroscopic procedures, it is preferable for the screen 22 to extend over the patient 12 from the foot 42 to the patient's mid abdomen region 44. The partition 36 may be formed from a flexible sheet of radiation-resistant material, permitting the screen 22 to fold like a curtain as the screen supports 34 slide along the table. It will be evident to those skilled in the art that other movable devices can be substituted for the sliding mechanism, including a screen that can rotate like an awning (not shown). Alternatively, the screen 22 may be constructed from rigid panels or segments. Also, screen segments may be hingedly attached like an accordion or rollably attached like a roll-top desk or a pool cover, or conformably attached like a Venetian blind.

As shown in FIG. 1, 5 and 6, 7 and 8, the screen 22 preferably includes at least one instrument port 46 through which physicians may operate on the patient 12 with procedural equipment (not shown), including threading a catheter through the port 46 and inserting the catheter into the patient 12. For fluoroscopic procedures in which a catheter is inserted into the patient 12, it is preferable to have access to the patient through ports 46 over the patient's groin region near the femoral vessels. Each access port 46 can be covered by a radiation-shielding cloak 48 that is attached to the screen 22 around catheters. The cloaks, generally 48, help protect the doctors operating around the x-ray table 14 from radiation scattering through their respective ports 46. The screen 22 may also have control ports 50, allowing connections and access to controls on the x-ray table (not shown). The x-ray table 14 may also have a user interface 52 external or internal to the screen 22. Access to the x-ray table's controls allows the operators to adjust the position of the table throughout the procedure. It may also permit the operators to control the position and orientation of the C-arm 32 and catheterization system monitors 54. As with other procedural equipment, the wall 20, screen 22, interface 24, and cloaks 48 can be sterilized. Alternatively to or in combination with removing the screen 22 from the x-ray table 14 and the interface 24 from the wall 20 for sterilization, such elements and the partition 36 and the skirt 40 may be covered by disposable, sterile covers (not shown).

With the radiation protection system 10 set in place, operators and other medical personnel in the operating region 16 are shielded from the x-ray emitter 18 and x-ray scattering during radiologic procedures. The radiation-shielding wall 20 separates the operating region 16 from the x-ray emitter 18 to protect the operators from exposure to most, if not all, primary radiation from the x-ray emitter 18 and from secondary radiation that could be scattered through the patient 12 or other sources. The radiation-shielding screen 22 is interposed between the doctors and the patient 12 to protect against most x-ray scattering from the patient 12 and the x-ray table 14. The radiation-shielding flexible interface 24 covers the opening 26 in the wall 20 and joins the wall with the x-ray table 14 and the screen 22 to protect against most radiation leaking into the operating region 16 when the x-ray table is moved.

Figure 2:
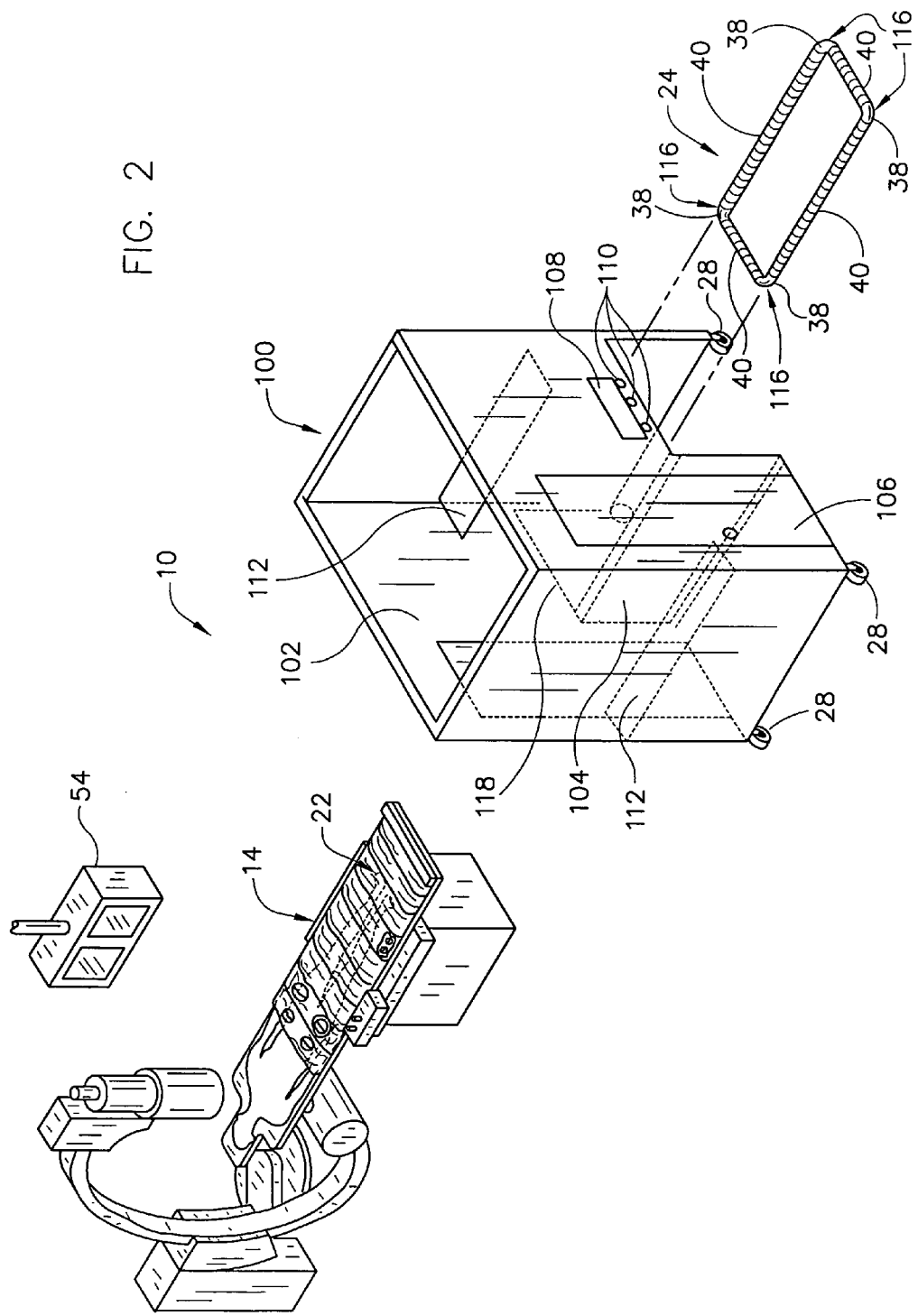
FIG. 2 illustrates a perspective view of an alternative embodiment of the radiation protection system in an unassembled state.
Figure 3:
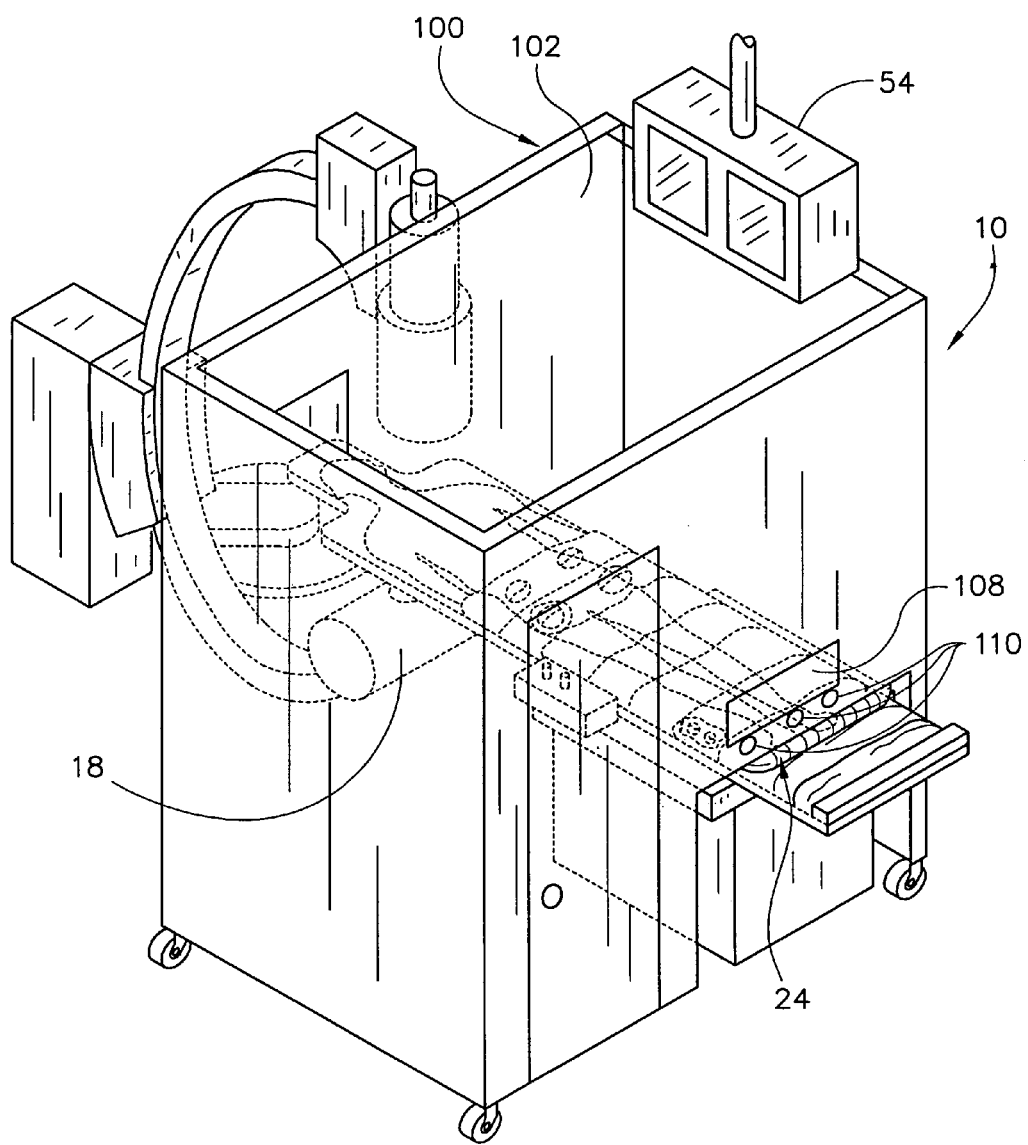
FIG. 3 illustrates a perspective view of the radiation protection system illustrated in FIG. 2 in an assembled state.
Figure 4:
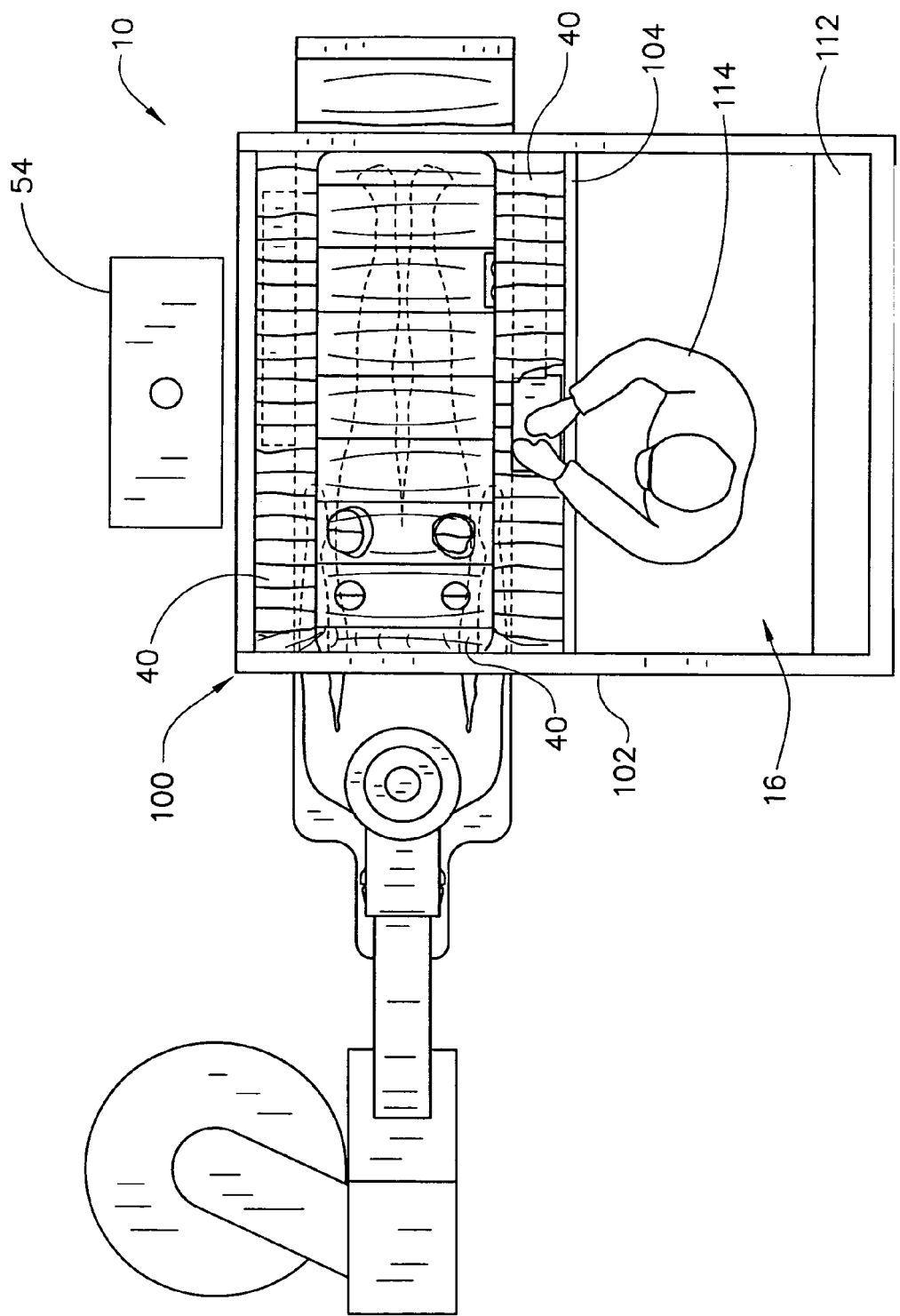
FIG. 4 illustrates a top plan view of the radiation protection system illustrated in FIG. 3.

FIG. 2 illustrates the unassembled sections of another embodiment of a radiation protection system 10. As in the first embodiment, the radiation protection system 10 includes a radiation-shielding screen 22 and a radiation-shielding flexible interface 24. In the second embodiment, the radiation protection system 10 has a radiation-shielding cubicle 100, and the flexible interface 24 is mounted circumferentially around the x-ray table 14. As illustrated in FIGS. 3 and 4, the cubicle 100 encloses the operating region 16 when the system 10 is assembled. The entire cubicle 100 can be constructed from well known radiation-blocking materials and it can be constructed to allow for repeated disassembly and reassembly for portability and storage. A first wall 102 is interposed between the personnel and the C-arm x-ray emitter 18. The first wall 102 is structurally and functionally similar to the radiation-shielding wall 20 in the first embodiment. Within the cubicle 100, the medical personnel region 16 preferably provides adequate space for two physicians to operate on the patient 12. A third cubicle wall 104, shown here as a half-wall, separates the personnel region 16 from the x-ray table 14.

As with the wall 20 in the previous embodiment, the cubicle 100 is preferably supported by a mobility device such as casters 28 that can be retracted when the cubicle is in place over the x-ray table 14. The cubicle 100 may also have at least one door 106. The cubicle 100 may contain access panels 108 for transferring equipment between the operating region 16 and the x-ray laboratory. The cubicle may also have tubing ports 110 for running catheters, tubes and other surgical equipment (not shown) from the patient 12 and the x-ray table 14 to other components in the x-ray laboratory. The cubicle may have its own ventilation system to maintain optimal ventilation and sterility, and may include shelves 112 for procedural equipment. Shelves 112 in the cubicle 100 may serve as a general staging table and shelves 112 suspended over the x-ray table 14 could serve as platform, allowing quick access to equipment by a doctor or other medical personnel 114. As in the previous embodiment, the cubicle 100 may also have monitors 54 to display fluoroscopic and other physiologic information, and the cubicle 100 may include an audio and/or video system for optimal communication between the medical personnel 114 and the rest of the laboratory.

In this embodiment, each corner 116 of the flexible interface 24 may be attached to the cubicle 100 through the flexible joint 38. As in the previous embodiment, the flexible radiation-resistant skirt 40 may be held between the joints 38 to cover an opening 118 in the wall 102 and to join the wall 102 with the x-ray table 14 and the screen 22. In the second embodiment, the skirt 40 may also circumferentially join the x-ray table 14 to the cubicle 100. As in the previous embodiment, the flexible joints 38 and skirt 40 permit the x-ray table 14 to be moved during the procedure. Extending and retracting the radiation screen 22 is performed in a manner that is similar to the previous embodiment, and transferring the patient 12 to and from the x-ray table is also performed a similar manner. In the second embodiment, the flexible interface 24 may be detached around its circumference so that the cubicle 100 can be moved and the screen 22 can be retracted to the foot 42 of the x-ray table 14.

FIG. 4 illustrates that these embodiments use much the same system for shielding operators and other medical personnel 114 from the x-ray emitter 18 and x-ray scattering when working in the personnel region 16 adjacent to the patient 12 on the x-ray table 14. In particular, operators are shielded from most x-ray radiation by isolating the personnel region 16 from the x-ray emitter 18 with the radiation-shielding wall 102 and the radiation-shielding flexible interface 24, covering the patient with a radiation-shielding screen 22 adjacent to the personnel region, and joining the wall 102 and the screen 22 with the flexible interface 24. The wall 102 and the flexible interface 24 isolate the personnel region 16 from the x-ray emitter 18. The flexible interface 24 attaches the x-ray table 14 to the wall 20, 102 through flexible joints 38, 116 and joins the screen 22 to the wall 20, 102 through a flexible radiation-resistant skirt 40. The second embodiment further isolates the operating region 16 with the half-wall 104 adjacent to the x-ray table 14 and uses the skirt 40 to circumferentially join the x-ray table 14 with the cubicle 100.

Figure 5:
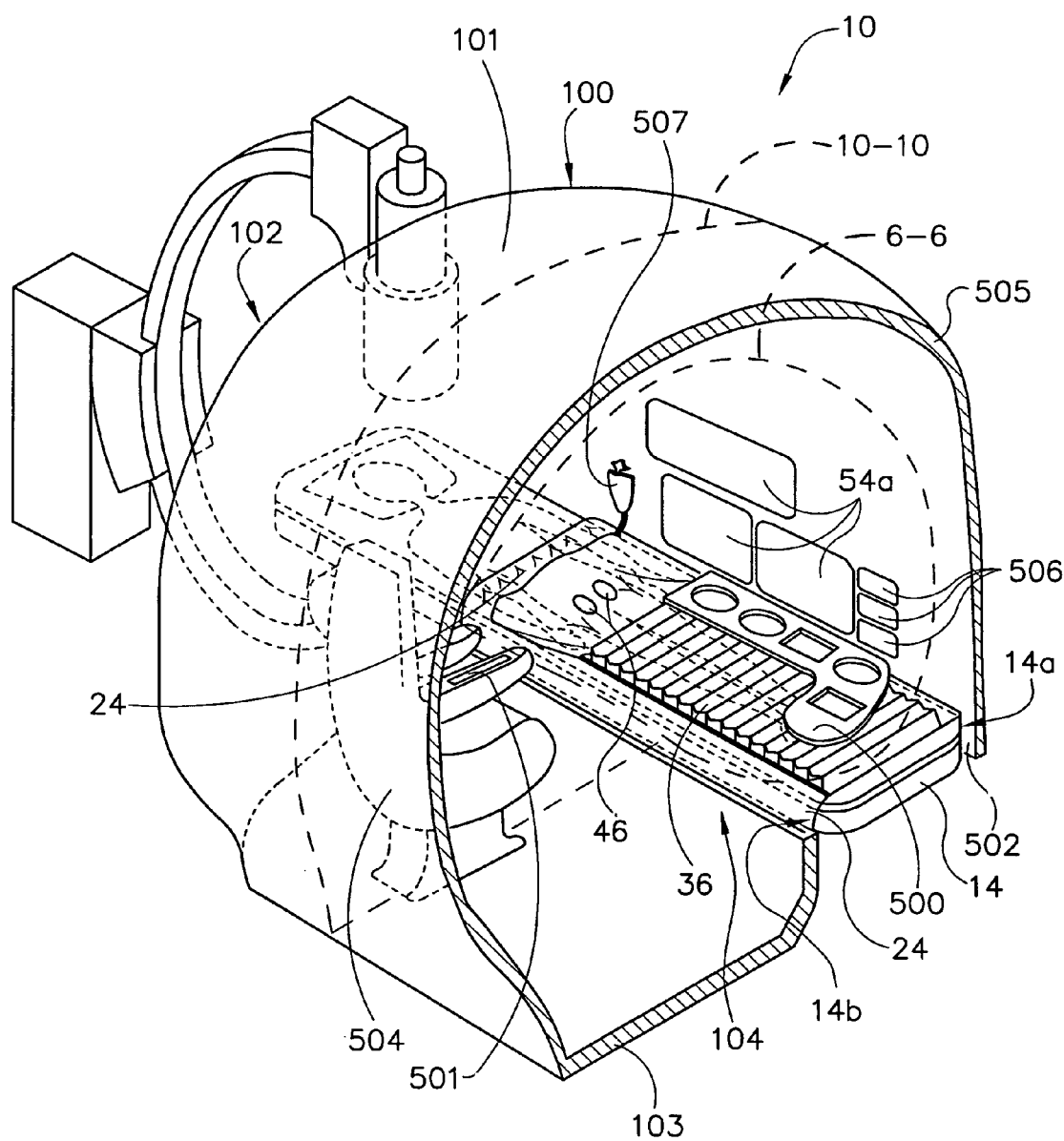
FIG. 5 illustrates a perspective view of another embodiment of the protection system and operations environment.

A preferred embodiment of the present invention is shown in FIG. 5 as a radiation protection system for shielding medical personnel from x-rays from an x-ray emitter while working on a patient, comprising an x-ray table 14 having a first side 14a, a second side 14b and a top surface, the top surface for supporting a patient 12; a radiation-shielding cubicle 100 having an interior defining a medical personnel region 16, the cubicle 100 having a ceiling 101, floor 103, a first wall 102 for separating the medical personnel from an x-ray emitter 18 disposed outside of the cubicle 100, a second wall 505 extending from one end of said first wall 102 adjacent to a first side 14a of the x-ray table 14 and a third wall 104 extending from the first wall 102 adjacent to a second side 14b of the x-ray table 14, the first wall 102 having an opening 26 for locating a portion of the x-ray table 14 into the interior of the cubicle; a radiation-shielding screen 22 attached to the x-ray table 14 for covering the portions of the patient and the top surface of the x-ray table located in the interior of the cubicle 100; a radiation-shielding flexible interface 24 for joining the x-ray table 14 to the cubicle 100, the flexible interface 24 having a flexible radiation-resistant skirt 40 sealing the opening 26; and an integrated procedural environment.

The present invention may include a control module 501 integrated into an operator's chair 504, however, the module 501 may be mounted in other suitable locations within the cubicle 100. The control module 501 may comprise controls for movement of the table 14, adjustments and movement of the chair 504 itself, as well as the C-arm, monitor 54a position, environmental conditions (lights, heating and air conditioning, etc.) and other various components. In addition, the control module 501 may comprise foot pedals on the chair 504 for more convenient access to various switches.

Figure 10:
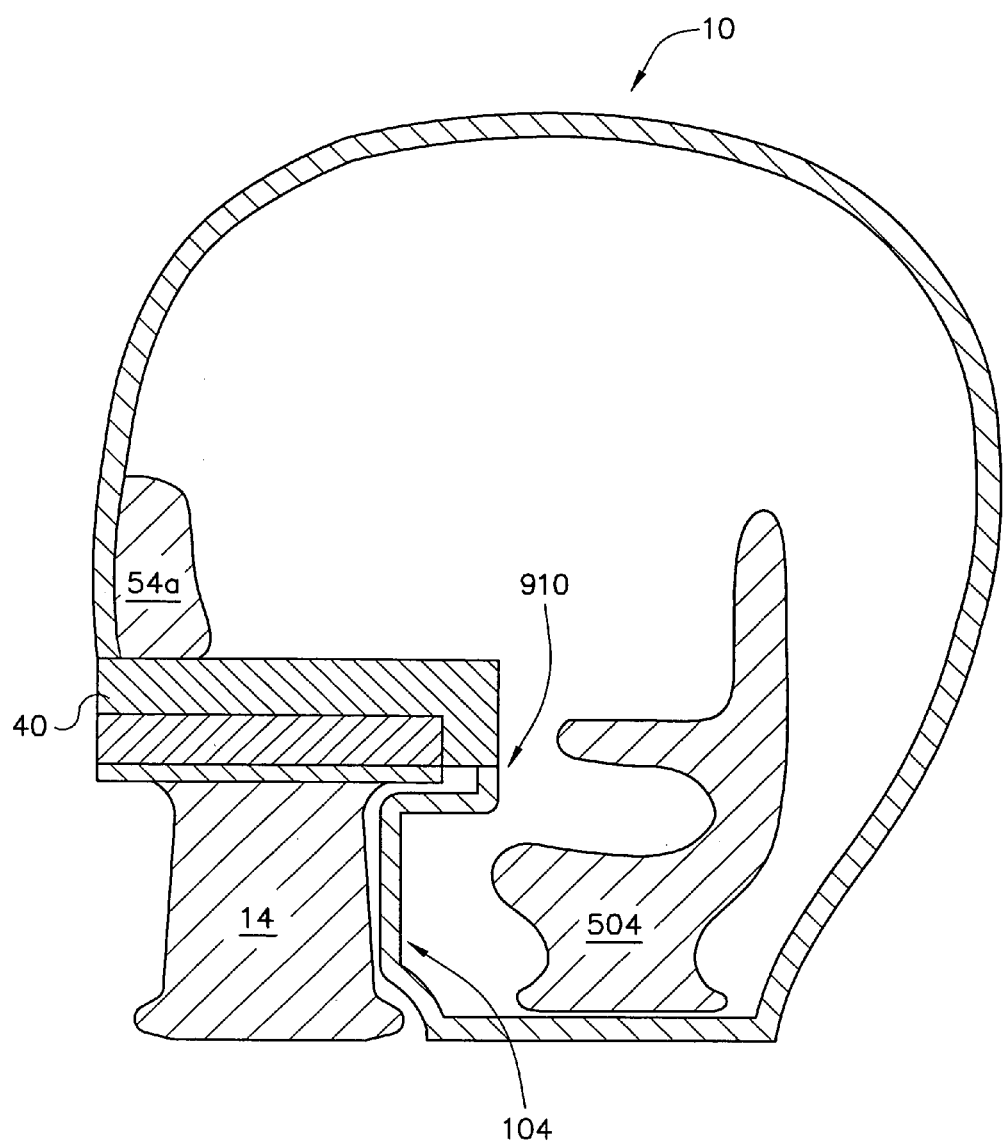
FIG. 10 shows a cross-section substantially along the line 10—10 of FIG. 5.

FIG. 10 depicts a cross-section of the system 10 along the line 10—10 in FIG. 5. As such, it illustrates another view of wall 104 disposed between the medical personnel and the table 14 as well as the connection 910 between the interface 24 and the wall 14 which is shown from above in FIG. 4.

The operator's chair 504 is designed for optimal comfort and ease of access to the patient so that the operator is positioned in an ergonomically designed adjustable chair positionable within the personnel region 16 with freedom of motion for hand movement control of all the operating functions of the integrated procedural environment at the touch of a finger, and to give the operator optimal ergonomic access to the patient and the medical equipment needed for the procedure. Alternatively, the chair 504 design may have a "stand-up" configuration as is known in the art to allow the operators to stand yet be supported orthopedically.

As shown in FIG. 5, the integrated procedural environment may also include the inside surface 502 of a cubicle 100 wall 505 across from the personnel region 16. As will be described herein, this surface 502 may be used to support various integrated elements including monitor displays 54a and staging platforms 500 for instruments. On the interior surface 502 of wall 505, fluoroscopic/cine screens and physiologic monitors 54a may be provided. In the integrated environment, the fluoroscopic monitors 54a may be placed in close proximity to the operator 114, which is in dramatic difference to previously available systems where the monitors are often positioned at an unnecessarily far distance and an orthopedically awkward angle relative to the operators. The interior surface 502 may support monitor displays 54a including fluoroscopic monitors, as well as physiologic monitors including, for example, EKG and blood pressure, for heart rate and oxygen measurements (pulse oximetry). The monitors may also include a display 506 of video from a patient video camera that includes both video as well as audio of the patient's head from a camera placed on the x-ray C-arm that tracks and angles towards the patient's head in order to keep visual monitoring of the patient, as well as two way microphone system to monitor and communicate with the patient during the procedure.

Figure 6:
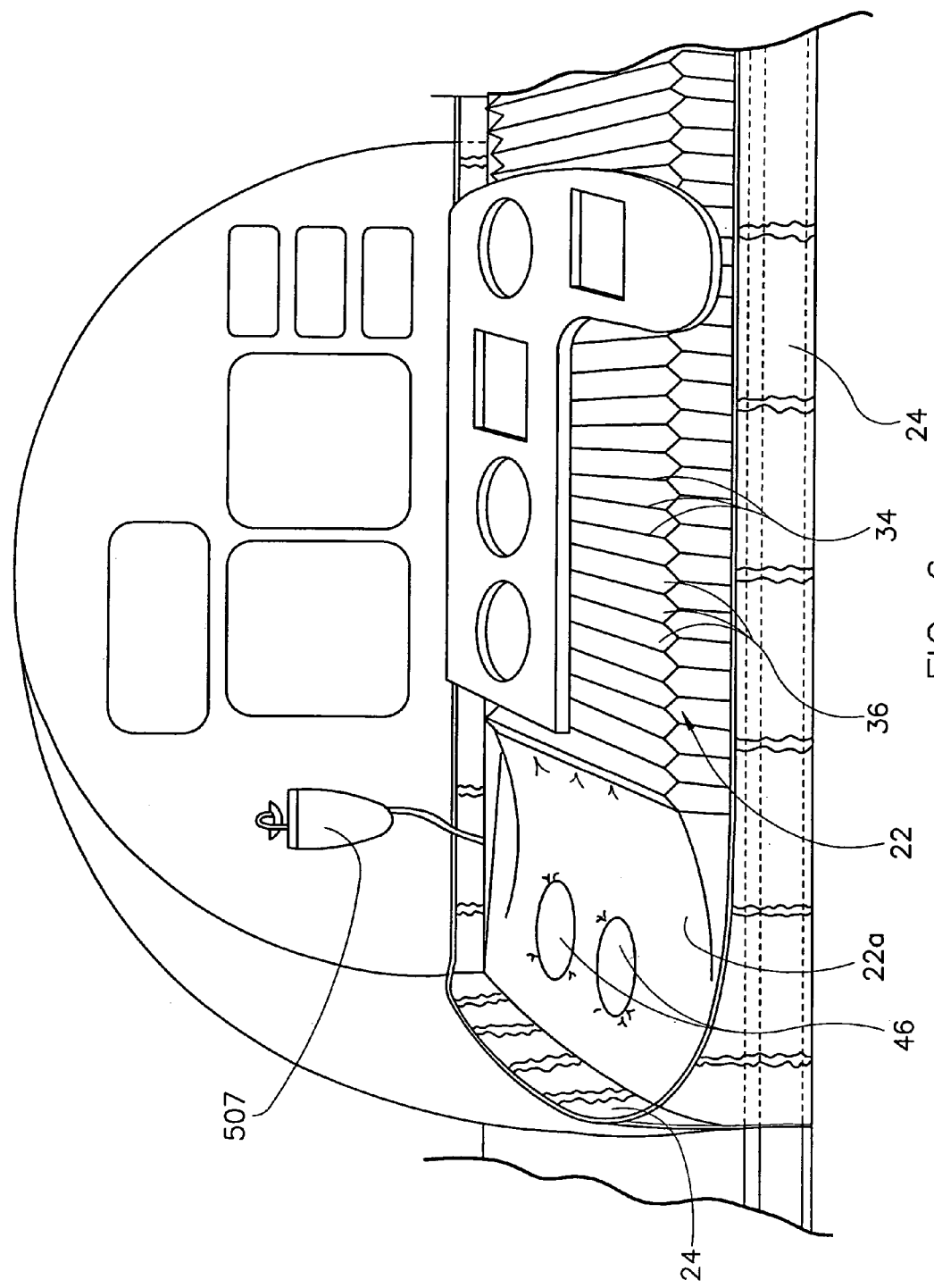
FIG. 6 illustrates a close up view of one embodiment of part of the operations environment within the cubicle area identified as 6—6 in FIG. 5.
Figure 7:
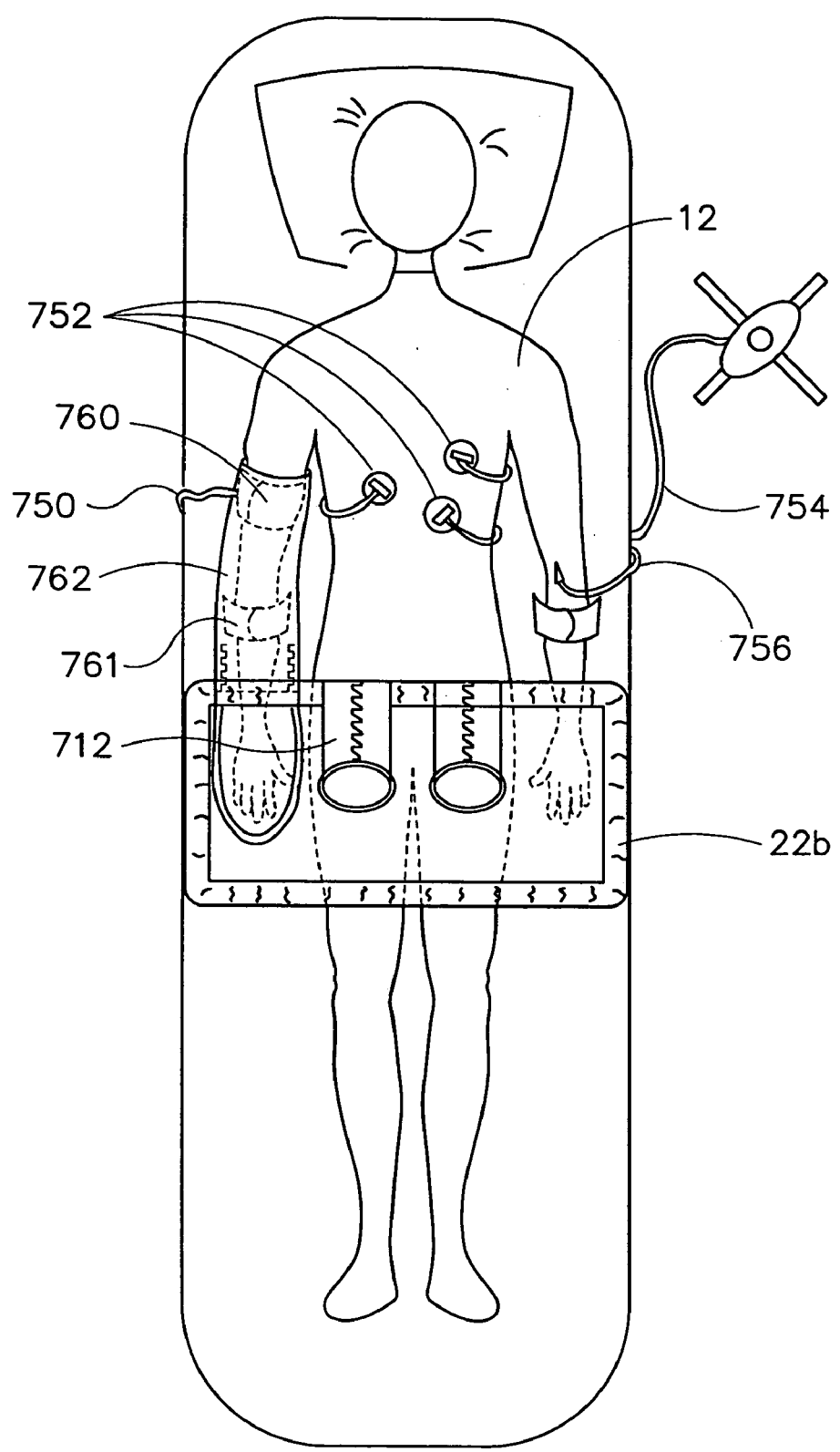
FIG. 7 illustrates a top-view of a patient positioned on the table of the present invention.

As shown in FIGS. 6 and 7, the radiation protection screen 22 may comprise a radiation protection vascular access drape or drape portion 22a composed of a soft, pliable, light, but radiation resistant material having ports 46 placed within the design of the overall screen 22 such that the position and size of the ports 46 allows full access to the correct aspect of the patient regardless of his size and weight. The shape and size of each port 46 are variable depending on the procedure being performed but in a preferred embodiment are substantially round and approximately 10 to 20 cm in diameter. The drape 22a may have a circumferential pleated portion 22b that may allow for attachment to the various other components including the flexible interface 24, table 14, cubicle 100, and the rest of the screen 22, if so constructed.

As shown in FIGS. 7 and 8, the drape 22a may also have one or more channels 710 in continuity with the cephalad (head) side of the ports 46 and overlaying the groin region of the patient. The channels 710 may be constructed of the same radiation resistant material as the drape 22a and may comprise a flap 712. The flaps 712 may comprise overlapping portions of drape material connected by hook and loop or other suitable fasteners. The channels 710 may be unflapped (opened) in order to allow a radiolucent area to be exposed in the occasional cases in which passage of the guide-wire from a needle through the groin region is difficult and requires fluoroscopic monitoring. Once the wire has been successfully advanced past this region, the flaps 712 can be reclosed to recomplete the radiation resistant seal over the channels 710.

This system may also include a radiation-shielding cloak 48, as shown in FIG. 9A. This cloak may be made of the same radiation resistant material as the drape 22a and constructed in a circular fashion with a radial slit 902 and a small diameter central orifice 904. This cloak 48 may be placed over a port 46 employed for the procedure and is applied once vascular access has been achieved and procedural equipment, such as a vascular sheath, is positioned in the patient. The cloak may then be opened at slit 902, encircled around the sheath and positioned to fully cover the port 46 so that the only component of the patient that is not fully covered by a radiation protection device is the minutely small diameter of the access sheath that exits through the protector orifice 904.

Additional components of the drape 22a may include a radiation shielding cloak 49 shown in FIG. 9B. This cloak 49 may be placed over an unused port 46. Cloaks (48, 49) may be covered or enclosed within a sterile drape which may have a hook and loop, adhesive strip or some other suitable fastener on one side that can then be attached to the drape 22a to maintain secure cloak (48, 49) positioning.

FIG. 7 also illustrates other novel aspects of the present invention. The table 14 of the present invention may incorporate conduit or similar built-in retention systems 750 for the consolidation and orderly routing procedural equipment including of the leads from various physiological monitoring sensors 752 attached to the patient 12.

Similarly, intravenous fluid bags 507 may be hung within the cubicle 100 and their lines 754 may be routed within conduit in the table 14 so as to facilitate the orderly and efficient maintenance of the procedural laboratory.

In addition, the table 14 may include at least one arm rest 762 which may have integrated restraints 761 and physiological sensors such as temperature, pulse meter, blood pressure cuff 760 and pulse oximeter. Leads from these sensors may be internally routed within the table 14 or routed within the table's conduit 750 as described above. The patient arm rest 762 may also serve to restrict hand and arm movement of the patient to aid in reducing contamination.

During fluoroscopic procedures, there are numerous disposable items employed including wires, sheaths, catheters, balloons, procedure dependent fluid administration, syringes, needles, hemostats, and many others. At present, such items are typically kept on a table behind the surgeon, with some items kept in the patient's groin or lap. The inefficiency of this system has been detailed in U.S. Pat. No. 5,586,163 which discloses and claims a novel platform and method for convenient access to such items. The integration of such a platform 500 into the present invention is illustrated in FIG. 5 attached to the inside surface 502 of the cubicle 100. Adapted in this way, the platform 500 will hold procedural equipment within the medical professional's reach in the operating region yet outside of the immediate surgical site and off of the patient.

In addition, the system 10 may include a radiation detector in operative connection with the fluoroscopy system for the automatic detection of radiation exposure above baseline levels and the subsequent automatic shutting down of the x-ray emitter and fluoroscopy system.

To use the invention, the patient would be prepped and draped and the radiation protection system 10 employed in the following manner: (1) The patient would be placed and sterily prepared on the table 14 in the standard fashion; (2) the sterily covered screen 22 is scrolled up from the foot of the table 14 to just below the patient's knees and the drape 22a (if used) is positioned from the patient's knees to waist or chest level; (3) the vascular access drape 22a is positioned such that the ports 46 are located over the right and left femoral vascular access regions of the patient; (4) the circumferential pleated connecting border 22b of the vascular access drape 22a is then connected to the flexible interface 24 as well as to the screen 22, if separate from the drape 22a; (5) a rectangular cloak 49, within a sterile drape, is placed over the unused vascular access ports; (6) vascular access is achieved; (7) a cloak 48 is placed around the inserted vascular sheath and positioned to fully cover the vascular access port 46 employed for the procedure.

In view of the foregoing, it will be seen that the several advantages of the invention are achieved and attained. The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, the wall 20 in the first embodiment can be curved or hinged to partially surround the operating region 16. As another example, the cubicle 100 can be wider to extend over the foot 42 of the x-ray table 14, thereby enlarging the operating region 16 within the cubicle 100. Thus, the breadth and scope of the present invention should not be limited by any of the above-described exemplary embodiments, but should be defined only in accordance with the following claims appended hereto and their equivalents.

What is claimed is:

1. A method of performing a medical procedure, said method comprising:
   providing a radiation-shielding cubicle having an interior defining a medical personnel region and including a first wall having an opening therein;
   locating the cubicle with respect to an x-ray table so a portion of the x-ray table extends through the opening into the interior of the cubicle; and
   separating medical personnel from an x-ray emitter disposed outside of the cubicle using the first wall to shield the medical personnel from radiation emitted by the x-ray emitter.

2. A method in accordance with claim 1 further comprising joining the x-ray table to the cubicle using a radiation-shielding flexible interface.

3. A method in accordance with claim 2 wherein said joining the x-ray table to the cubicle using a radiation-shielding flexible interface comprises joining the x-ray table to the first wall using the radiation shielding flexible interface.

4. A method in accordance with claim 1 further comprising sealing the opening in the first wall using a flexible radiation-resistant skirt.

5. A method in accordance with claim 1 further comprising circumferentially joining the x-ray table to the cubicle using a flexible radiation-resistant skirt.

6. A method in accordance with claim 1 further comprising attaching a radiation-shielding screen to the x-ray table so the radiation-shielding screen covers a portion of a patient supported by the x-ray table and covers a portion of a top surface of the x-ray table.

7. A method in accordance with claim 6 further comprising joining the first wall to the radiation-shielding screen using a flexible radiation-resistant skirt.

8. A method in accordance with claim 6 wherein the radiation-shielding screen has at least one port for facilitating access to the patient, said method further comprising:
   inserting procedural equipment through the port to access the patient with the procedural equipment; and
   performing a medical procedure on the patient using the procedural equipment.

9. A method in accordance with claim 8 further comprising positioning a cloak over the port to create a substantially radiation-resistant seal over the port and around the procedural equipment.

10. A method in accordance with claim 6 wherein the radiation-shielding screen has at least one port for facilitating at least one of connection and access to controls for at least one of the x-ray table, the x-ray emitter, and a catheterization system monitor, said method further comprising accessing the controls using the port to control at least one of the x-ray table, the x-ray emitter, and the catheterization system monitor.

11. A method in accordance with claim 1 further comprising:
   detecting radiation levels within the radiation-shielding cubicle; and
   terminating operation of the x-ray emitter when the detected radiation levels are above a predetermined level.

12. A method in accordance with claim 1 further comprising monitoring portions of the patient located outside the radiation-shielding cubicle from inside the radiation-shielding cubicle using a video camera.

13. A method in accordance with claim 1 further comprising communicating with the patient from inside the radiation-shielding cubicle using a two-way microphone system.

* * * * *